(12) United States Patent
Scatizzi

(10) Patent No.: US 8,925,356 B2
(45) Date of Patent: Jan. 6, 2015

(54) APPARATUS AND PROCESS FOR PERFORMING OPTICAL READINGS ON PACKAGED TEXTILE MATERIAL SUBJECTED TO DYEING

(75) Inventor: Mario Scatizzi, Prato (IT)

(73) Assignee: Tecnorama S.r.l., Prato (IT)

( * ) Notice: Subject to any disclaimer, the term of this patent is extended or adjusted under 35 U.S.C. 154(b) by 432 days.

(21) Appl. No.: 13/142,066

(22) PCT Filed: Mar. 10, 2010

(86) PCT No.: PCT/IT2010/000100
§ 371 (c)(1),
(2), (4) Date: Jun. 24, 2011

(87) PCT Pub. No.: WO2010/109507
PCT Pub. Date: Sep. 30, 2010

(65) Prior Publication Data
US 2011/0271463 A1 Nov. 10, 2011

(30) Foreign Application Priority Data
Mar. 27, 2009 (IT) .................. FI2009A0062

(51) Int. Cl.
| *D06P 5/00* | (2006.01) |
| *D06B 23/10* | (2006.01) |
| *D06B 23/26* | (2006.01) |
| *G01N 21/55* | (2014.01) |
| *G01N 21/84* | (2006.01) |
| *G01N 21/952* | (2006.01) |

(52) U.S. Cl.
CPC . *D06B 23/10* (2013.01); *D06P 5/00* (2013.01); *D06B 23/26* (2013.01); *G01N 21/55* (2013.01); *G01N 21/84* (2013.01); *G01N 21/952* (2013.01)
USPC .............. 68/12.07; 68/12.02; 8/400

(58) Field of Classification Search
CPC .......... D06P 5/00; D06B 23/10; D06B 23/26; G01N 21/55; G01N 21/84; G01N 21/952
USPC ........ 68/12.02, 12.07; 8/400; 69/12.02, 12.07
See application file for complete search history.

(56) References Cited

U.S. PATENT DOCUMENTS 2,109,893 A * 3/1938 Abbott ........................... 68/189
3,181,318 A * 5/1965 Wyatt ............................. 68/150
(Continued)

FOREIGN PATENT DOCUMENTS

| EP | 319361 | 6/1989 |
| EP | 325529 | 7/1989 |
| EP | 1 288 364 A | 3/2003 |
| GB | 2050002 | 12/1980 |
| JP | 61105432 | 5/1986 |

(Continued)

*Primary Examiner* — Alexander Markoff
(74) *Attorney, Agent, or Firm* — McGlew and Tuttle, P.C.

(57) ABSTRACT

Apparatus for performing optical readings on yarn spools subjected to dyeing in a dyeing tank or machine (1) in which a spool (6) provided with a pierced axial shaft (6A) is placed with the said shaft on the outlet of a feedpipe (IM) of a circuit that feeds a dyeing bath in the same tank or machine (1), so that the dyeing bath enters the dyeing tank or machine (1) passing by the feedpipe (IM) through the shaft (6A) and is subsequently collected through collecting conduit (IR) of the same feeding circuit. The apparatus comprises optical detection means connected with electronic processing means and the said optical detection means comprise a detector (9) with an optical window (92) located inside the dyeing tank or machine (1), a base of the spool (6) being cyclically put in contact with said optical window (92), periodically, the said spool being moved towards the optical window (92) by means of an actuator (7) which, cyclically, moves the said shaft (6A) the said base of the spool (6) towards a part (2) of the dyeing tank or machine (1) where the said optical window (92) is located.

7 Claims, 4 Drawing Sheets

(56) References Cited

U.S. PATENT DOCUMENTS

| | | | |
|---|---|---|---|
| 3,573,476 A | 4/1971 | Falcoff et al. | |
| 3,806,256 A | 4/1974 | Ishak | |
| 3,807,872 A | 4/1974 | Pronier | |
| 3,986,778 A | 10/1976 | Mathisen et al. | |
| 2004/0250575 A1* | 12/2004 | Ronchi | 68/189 |
| 2010/0011516 A1* | 1/2010 | Scatizzi | 8/400 |
| 2011/0271463 A1* | 11/2011 | Scatizzi | 8/400 |

FOREIGN PATENT DOCUMENTS

| | | | |
|---|---|---|---|
| JP | 1006164 | | 1/1989 |
| JP | 5098557 | | 4/1993 |
| WO | WO 99/66117 | | 12/1999 |
| WO | WO 03/102288 | | 12/2003 |
| WO | WO 2005/040482 | | 5/2005 |
| WO | WO 2008/023396 | | 2/2008 |
| WO | WO2008/078345 | * | 3/2008 |
| WO | WO 2008/078345 | | 7/2008 |

* cited by examiner

APPARATUS AND PROCESS FOR PERFORMING OPTICAL READINGS ON PACKAGED TEXTILE MATERIAL SUBJECTED TO DYEING

The present invention relates to an apparatus and a process for performing optical readings on packaged textile material subjected to dyeing.

More particularly, the apparatus and the process subject of the present invention allow control of depletion, that is to say of absorbance, of the single colouring or dyeing agents present in a dyeing bath.

Optical systems and processes based on transmittance spectrophotometry are known in this field. The concentration of single colouring agents present in the bath solution, that is in the dyeing bath, is measured by means of said systems, by directing a beam of light having known features through it. Part of the light is absorbed by the substances present inside the fluid, whereas the remaining part is transmitted to the spectrophotometer which detects its amount and its features. These constitute information used to determine the residual quantities of the single colouring agents present in the bath solution according to the well-known Beer-Lambert law.

It is also known that, whatever the specific algorithm used for processing the above information, the exact determination of the single colouring agents present in the dyeing bath is still an unsolved problem from a practical viewpoint given the innumerable chemical and dyeing typologies of the various colouring agents used in textile industry.

When using known optical systems for online transmittance reading, there are remarkable practical difficulties in determining the concentration of single colouring agents present in a dyeing bath with sufficient exactness, with particular reference to the determination of very small concentrations, as well as to those exceeding given values. In practice, the known optical systems have proved to be ineffective in the control of bath solutions containing colouring agents whose concentrations are, in their value, external to a given range. In other terms, optical control systems currently available on the market are substantially unusable for practical purposes whenever the concentrations concerned assume values which are not within a given range, that is to say when bath solutions are too diluted or too concentrated.

Further drawbacks arising from the use of known optical systems are connected with the remarkable inexactness in the results obtained from readings carried out on bath solutions containing heterogeneous colouring agents, that is of different chemical classes and with the substantial impossibility of distinguishing two different colours of the same kind (two reds, two yellows or two blues present in the same bath solution).

Further inconveniences arise from state changes, that is colour changes of the single colouring agents when the pH, salinity or temperature in the solution vary, as normally happens during the dyeing cycle: in fact, in this case, the transmittance optical control does not guarantee correct and homogeneous readings, since chromatic changes may occur and the bath solution may become torpid.

Moreover, the control carried out on dispersions and opalescent baths is very difficult as the light transmission through the liquid is altered, because part of the light is deviated by the dispersed particles within the liquid. This leads to erroneous evaluations, that is the spectrophotometer evaluations can be wrong.

Examples of apparatuses for carrying out controls by transmittance readings are described in EP325529, FR2399066, FR2307074, FR2443524, GB2050002, JP1006164, EP319361, WO2005/040482, WO2003/102288, EP319361, US3807872, WO99/66117, JP5098557 and JP61105432.

PCT/IT2007/171 (WO2008/023396) and PCT/IT2007/178 (WO2008/078345) disclose devices for carrying out control of the depletion, that is of the absorbance of single colouring agents on textile specimens, instead of on the dyeing bath. According to the techniques disclosed in PCT/IT2007/171 (WO2008/023396) and PCT/IT2007/178 (WO2008/078345) a textile specimen, subjected to dyeing is positioned in a suitable chamber and immersed and let flow in a dyeing bath. The dyeing bath flowing in the dyeing tank is let flow in the chamber where the textile specimen is positioned. Control of the depletion of colouring agents is carried out by reflectance optical reading on the specimen material, by cyclically approaching it to an optical detector connected to corresponding electronic means for processing the received signals.

As in the case of readings carried out on the dyeing bath, the reading carried out on the textile specimen subjected to dyeing is an indirect reading.

It is therefore still felt the need to carry out a direct control, that is a direct optical reading on the textile material subjected to dyeing, especially if the textile material is a "packaged" one, like, for example, yarns wound on spools, in order to achieve more reliable results by means of optical reading.

The main aim of the present invention is to eliminate or, at least, to remarkably reduce the inconveniences caused by indirect optical readings carried out on textile materials subjected to dyeing in order to render the results obtained by means of optical readings much more reliable, with particular reference to packaged textile materials.

These results have been achieved, according to the present invention, by adopting the idea of realising an apparatus and carrying out a method having the features described in the independent claims. Further features of the present invention are the subject of the dependent claims.

Thanks to the present invention, it is possible to correctly execute depletion controls of the single colours (red, yellow, blue) in a dyeing bath, whatever the class or kind of the colouring agents used, by directly acting on the textile material positioned in the tank or dyeing machine. Moreover, it is possible to carry out repetitive readings with sufficiently elevated frequency so that they can be considered as "dynamic", that is to say continuous. Moreover, an apparatus according to the present invention is easy to build, economic and reliable even after long operating periods. The structural and functional simplicity of the apparatus subject of the present invention allow the reduction of its cost and a greater diffusion of control systems in dyeing of textile materials.

These and further advantages and features of the present invention will be better understood thanks to the following description and to the enclosed drawings provided by way of example but not to be considered in a limitative sense, wherein.

Figure 1:
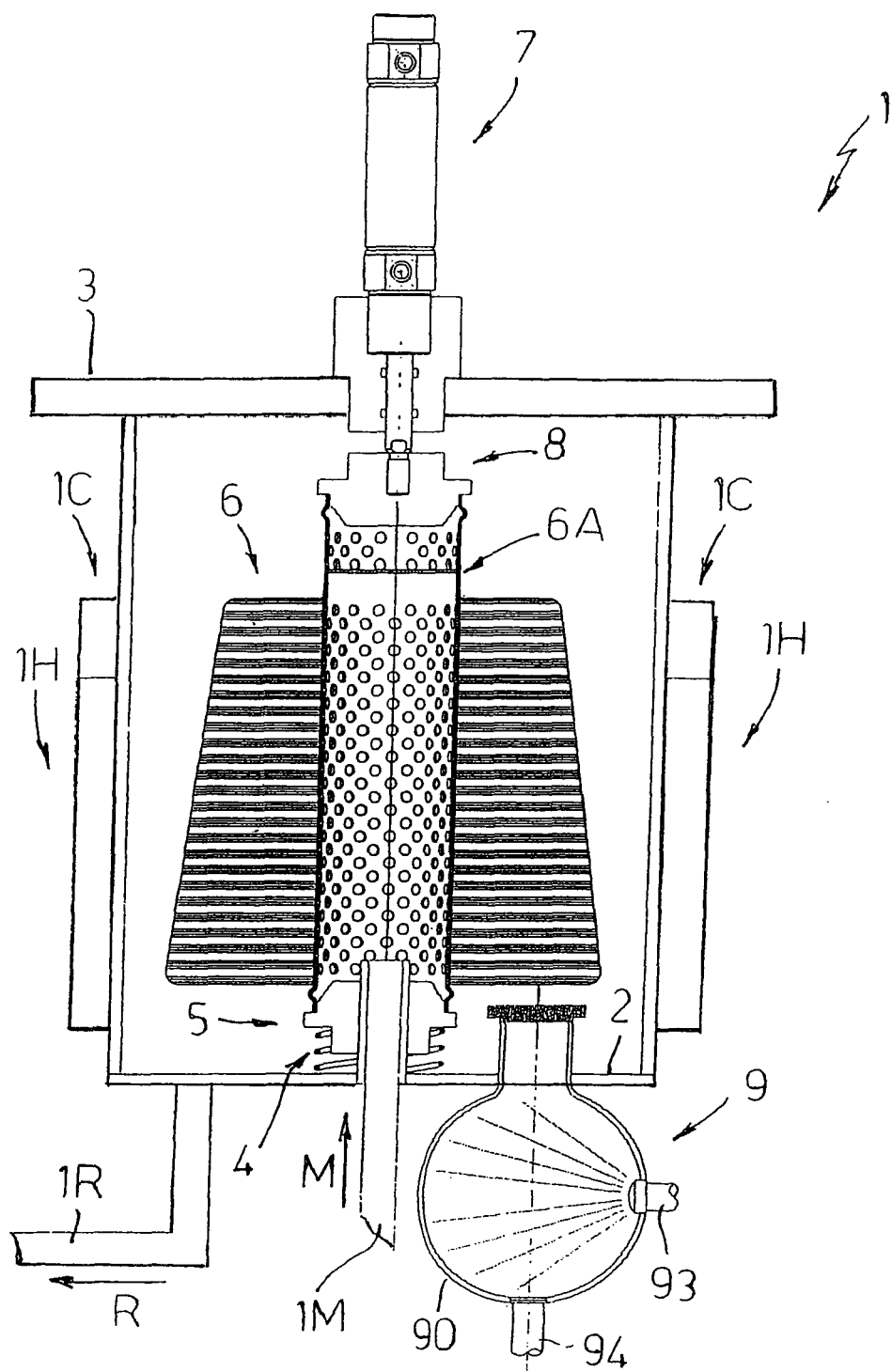
FIG. 1 shows a schematic vertical section view of a dyeing machine according to the present invention inside which a yarn spool is positioned, in a phase in which the optical reading does not take place.

Reduced to its essential structure and with reference to the figures of the enclosed drawings, a dyeing machine according to the present invention comprises a tank (1) with a base (2)

and a lid (3). A dyeing bath flows inside the tank (1), the dyeing bath being fed by a circuit comprising a feeding pipe (1M) and a collecting conduit (1R) between which a pump (P) is disposed. The said feeding pipe (1M) passes centrally through the base (2) of the tank, projects beyond said base, passes inside the tank. The length of said feeding pipe disposed inside the tank constitutes the end part of the same feeding pipe. The collecting conduit (1R) of said circuit extends from the base (2) of the tank (1) at a predetermined distance of the central axis thereof. In this way, the dyeing bath is let flow continuously and centrally fed into the tank (1) through a feeding pipe (1M) and laterally collected through a collecting conduit (1R) as indicated by arrows "M" and "R". A flow-meter (1F) and a thermometer (1T) are inserted on the feeding pipe Other sensors (i.e for detection of the dyeing bath pH) can be inserted in said feeding circuit or in the tank (1) according to modalities which are per se known and have therefore not been described in more detail.

A spring (4) is mounted on the internal side of the base (2) coaxial and external to the outlet of the feeding pipe (1M) inside the tank (1) and a tubular support (5), whose function is described below, bears on the spring (4). Said support (5) is also coaxial and external to the end part of the feeding pipe (1M) passing inside the tank (1) and exhibits an annular projection (50) which allows its stable positioning onto the upper base of the spring (4). The lower base of the latter is located on the internal side of the base (2) in the above mentioned position. Therefore, said support (5) is an elastic support which is normally distanced from the base (2) of the tank (1). However, the support (5) can be moved against the base (2) by exerting a thrust on it sufficient to overcome resistance of the spring (4).

As shown in the figures of the enclosed drawings, said support (5) exhibits an upper part (51) and a lower part (52) separated by the annular projection (50), the upper part (51) being truncated-conical shaped and the lower part (52) being cylindrical.

In the embodiment shown in the figures of the enclosed drawings, the lower part (52) of said support (5) is internal to the spring (4), that is, it is located between the outlet of the feeding pipe (1M) and the spring (4).

A pierced axial shaft (6A), around which a spool (6) to be dyed in the tank (1) is wound, is positioned onto said support (5), that is on the upper part (51) thereof. The diameter of said shaft (6A) is such as to allow its external and coaxial positioning on the end part of the feeding pipe (1M), and it is such that the truncated conical upper part (51) of the support (5) is internal to the shaft (6A) so that the its lower base is located on the annular projection (50) of the support (5). Positioning of the shaft (6A) is facilitated by the fact that the upper part (51) of the latter is truncated-conical.

A vertical-axis actuator (7) is provided on the lid (3) of the tank (1), the said vertical-axis actuator being axially aligned with the support (5) and exhibiting a stem, oriented towards the base (2) of the tank (1). A buffer (8) is fixed to the said stem. The said buffer, in the embodiment shown in the enclosed drawings, is identical to the afore-mentioned support (5) but is oriented in the opposite direction. In other terms, the buffer (8) exhibits a truncated conical upper part (81) and a cylindrical lower part (82) which are separated from each other by an annular projection (80).

In its operating position, (as shown in FIG. 1 and in FIG. 2), the lower part (81) of the buffer (8) is internal to the shaft (6A), whereas its upper part (82) is turned towards the lid (3) of the tank (1) and the upper base of the shaft (6A) is in contact with the annular projection (80) of the buffer (8).

Moreover, the base (2) of the tank (1) exhibits an opening for an optical detector (9). Said opening is positioned laterally with respect to the end part of the feeding pipe (1M).

Figure 2:
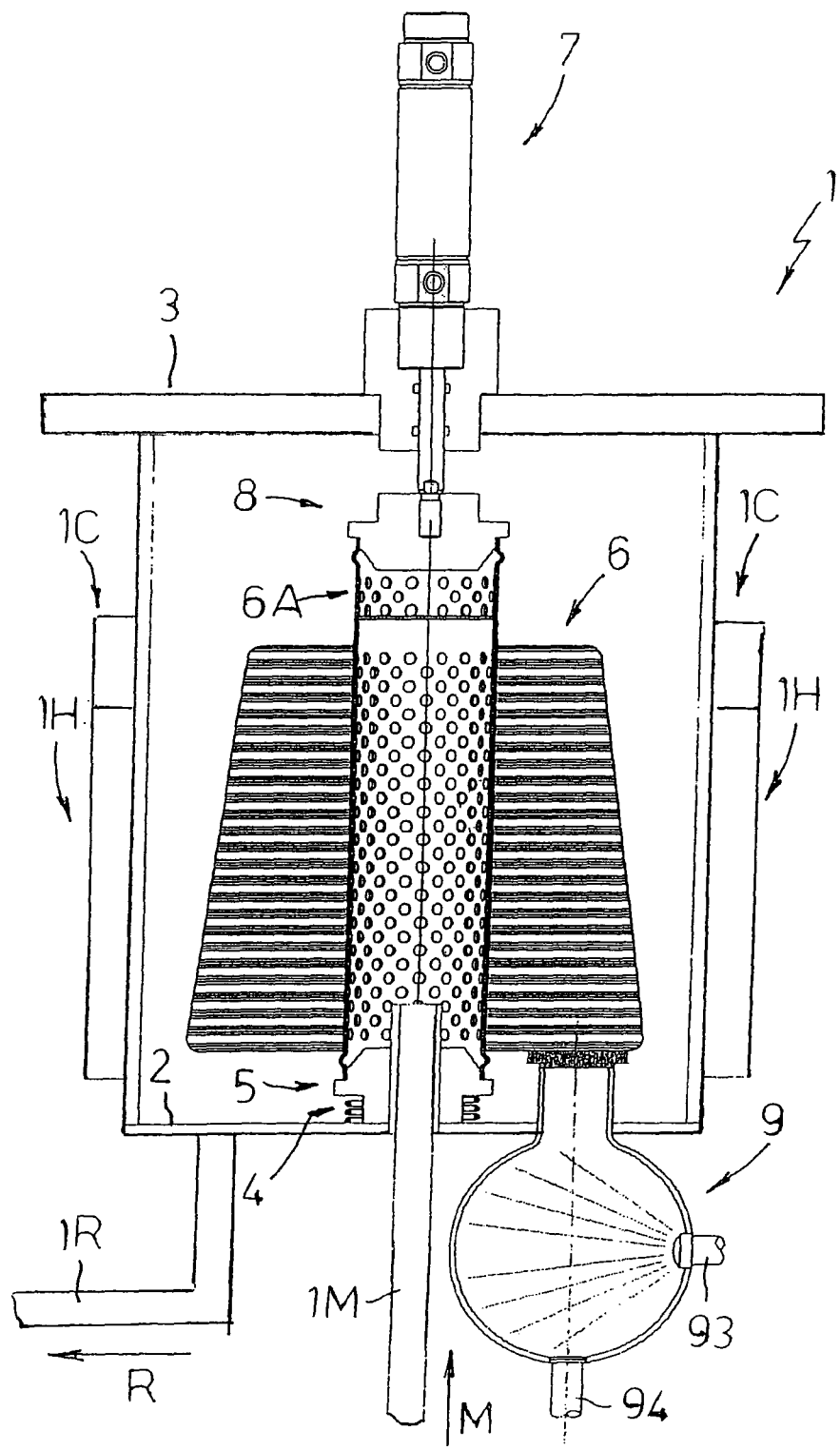
FIG. 2 shows the same dyeing machine of FIG. 1 during an optical reading phase.
Figure 3:
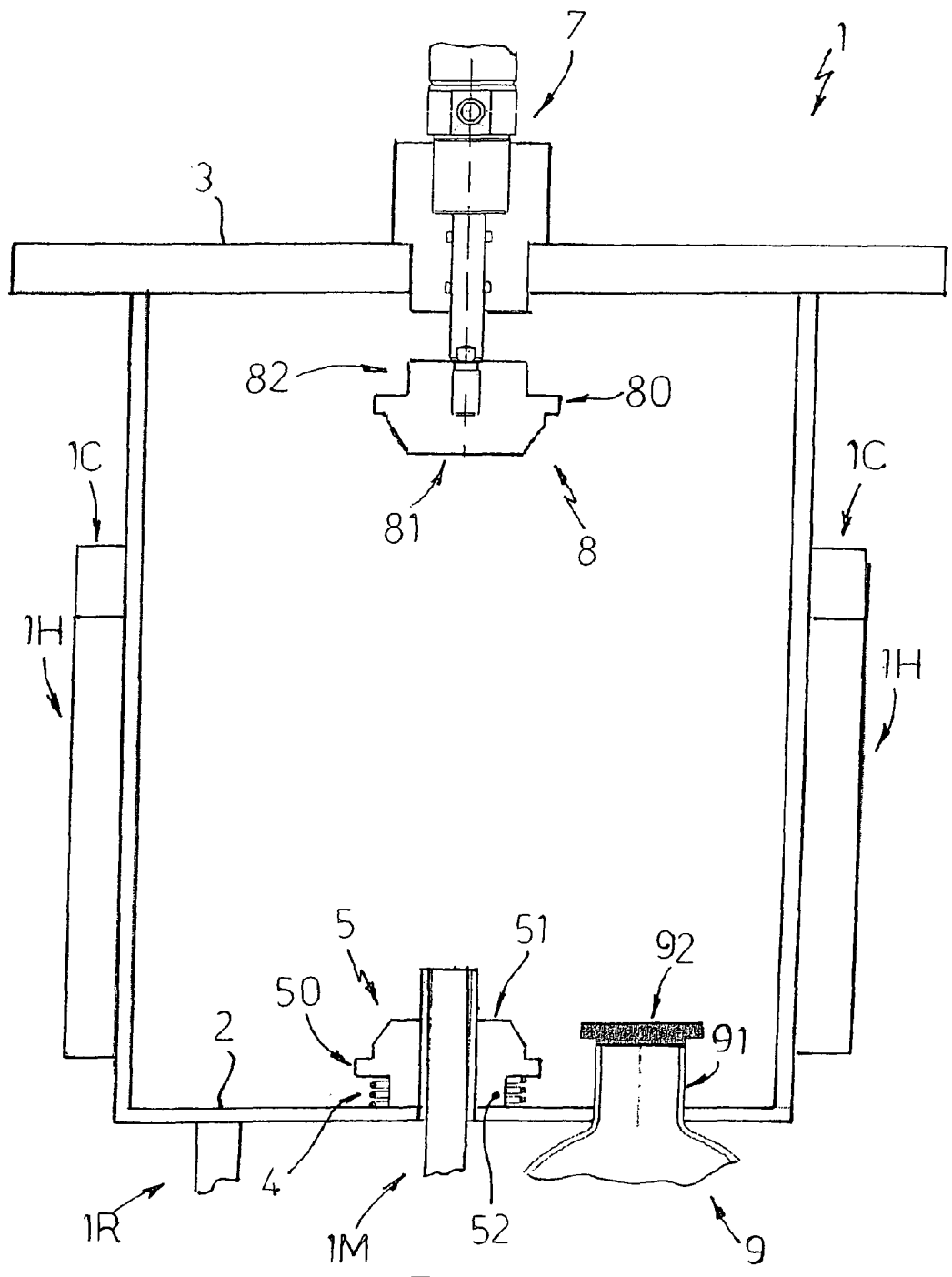
FIG. 3 shows a view which is analogous to that of FIG. 2 in which the spool is not shown to better highlight the inside of the dyeing tank.

Said optical detector (9) exhibits a body (90), preferably spherical, with a vertical collar (91) which is internal to the tank (1) and ends with a horizontal optical window (92). Moreover, the optical detector (9) exhibits an optical fiber (9) connected to a luminous source (L) which projects a luminous beam generated outside the body (90) through the window (92) and an optical probe (92) in a diametrically opposed position whose function is described in the following. The height of the collar (91) of the detector (9) is such that the optical window (92) is in contact with the lower base of the spool (6) when the lower part of the support (5) is in contact with the base (2) of the dyeing tank (as shown in FIG. 2). Vice versa, when the support (5) is lifted (as shown in FIG. 1) said optical window (92) is distanced from the spool (6) in a position underneath the lower base thereof. As shown in the figures of the enclosed drawings, the collar (91) and the optical window (92) of the detector (9) are internal to the tank (1).

In practice, when the actuator (7) is not activated (as shown in FIG. 1) so that the support (5) is moved upwards by the spring (4), the window of the detector (9) is distanced from the lower base of the spool (6) and, when the actuator (7) is activated (as shown in FIG. 2), so that the support (5) is moved downwards by the spring (4), the window (92) of the detector (9) is in contact with the lower base of the spool (6).

Since said body (90) is spherical and due to the presence of the vertical collar (91) which connects the window (92) to the body (90) the luminous flow passing through the optical window (92) is uniform, that is to say it is diffused and not concentrated.

As further described below, said luminous flow is produced when the spool (6) is lowered and its lower base is positioned in contact with the window (92) of the detector (9).

The optical fiber (94) of the detector (9) is connected to the spectrophotometer or to the colorimeter (10) and transmits to the latter the light reflected from the spool (6) through the optical window (92) when the spool is lowered, as previously mentioned.

Figure 4:
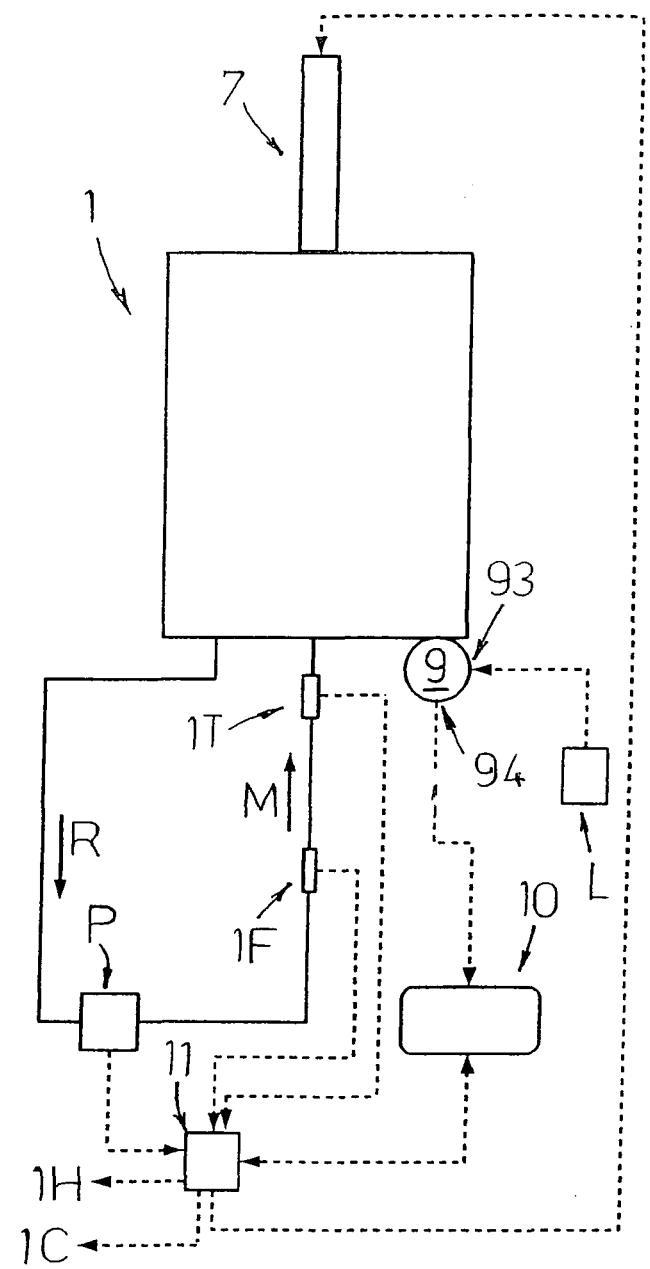
FIG. 4 shows a simplified block diagram representing a circuit in which the machine of FIGS. 1 and 2 is inserted.

As shown in the diagram of FIG. 4, the spectrophotometer (10), the sensors (1F, 1T), the pump (P) and the actuator (7) are connected to a per se known programmable electronic processing unit for controlling the actuator (7) and the pump (P) and for processing the output signals emitted by the sensors (1T) and (1F) and by the spectrophotometer or the colorimeter (10). By means of a programme and according to the values detected by a sensor (IT), said processing unit (11) controls a heating unit (1H) and a cooling unit (10) by means of which the dyeing bath temperature is kept at a predetermined value.

The tank (1), the sensors (1F) and (IT), the units (1H) and (1C), the pump (P) and the spectrophotometer or colorimeter (10) are per se known.

The apparatus described above functions as follows.

The lid (3) is removed and the spool (6) is positioned inside the tank (1), with the lower base of the shaft (6A) placed onto the annular projection (50) of the elastic support (5) and with the end part of the feeding pipe (1M) positioned inside to the shaft (6A). The lid (3) is reinstalled so as to close the tank (1) such that the upper base of the shaft (6A) is in contact with the annular projection (80) of the buffer (8). At this point, the feeding process for the dyeing bath starts by enabling the pump (P) which allows the dyeing bath to flow inside the feeding pipe (1M) and in the collecting conduit (1R). In particular, the dyeing bath continuously passes among the fibres of the spool (6) flowing from the pipe (1M) and through the holes of the shaft (6A), thus entering the tank (1), and is subsequently collected by the collecting conduit (1R). The unit (11) cyclically controls the operation of the actuator (7) and determines the lowering of the spool (6). More particularly, the actuator (7) moves the shaft (6A) towards the base (2) of the tank (1) by acting on the buffer (8). The run of the actuator (7) is such that, when the spool (6) is in its lowered position, its lower base (major base with reference to the embodiment shown in FIG. 1 and in FIG. 2) is in contact with the optical window (92) of the detector and the lower part (52) of the support (5) is in contact with the base (2) of the tank (1). When the spool (6) is in the above mentioned position, the spectrophotometer (10) controls the lighting device (93), so the lower base of the spool (6) is lighted in correspondence of the window (92). The probe (94) receives the light reflected by the spool (6) through the optical window (92) and transmits the corresponding luminous signal to the spectrophotometer (10) which processes it. The processing of the luminous signal transmitted by the detector (9) to the spectrophotometer or to the colorimeter (10) is carried out according to known algorithms, so they will not be described in more detail, and said algorithms allow evaluation of the absorbance of the single colouring or dyeing agents in the material of the yarn spool (6), that is, their depletion, even when the pH or the temperature or the salinity of the dyeing bath vary. The reading, that is the spectroscopic analysis of the signal sent by the detector (9) to the spectrophotometer (10), involves directly the material dyed in the tank. In other terms, since the material of the spool (6) is put directly in contact with the optical window of the detector (9), errors typical of devices in which readings are carried out on the dyeing bath do not occur and the reading is particularly reliable as it is a direct reading, not an indirect reading. During the reading phase, the material of the spool (6) is pushed and held on the window (92) of the detector (9) so as to avoid any interferences of the dyeing bath on optical readings. Moreover, the reading is carried out by reflectance and, during reading, the dyeing bath continues to flow. In other terms, a reading performed as described above does not alter or hinder the real dyeing process which takes place inside the tank (1). At the end of said reading, the unit (11) operates the actuator (7) to bring the spool back into the starting position. As previously said, during a dyeing process it is possible to carry out more repetitive readings with sufficiently high frequency so that they can be regarded as "dynamic", that is continuous.

It goes without saying that the motion of the spool (6) from and to the optical window (92) can take place in any other suitable way.

In the embodiment shown in FIG. 1 and in FIG. 2 the spool (6) is a conical spool with its major base turned downwards.

In practice, the construction details may vary in any equivalent way as regards the shape, dimension, disposition of elements, nature of the used material without nevertheless departing from the scope of the adopted solution idea and thereby remaining within the limits of the protection granted to the present patent.

The invention claimed is:

1. An apparatus for performing optical readings on yarn spools subjected to dyeing in a dyeing tank or machine, the apparatus comprising:
   a spool with a pierced axial shaft placed in the dyeing tank or machine, said pierced axial shaft being on an outlet of a feedpipe of a feeding circuit that feeds a dyeing bath in the dyeing tank or machine, such that the dyeing bath enters the dyeing tank or machine passing by the feedpipe through the pierced axial shaft and is subsequently collected through a collecting conduit of the feeding circuit;
   a reflectance measuring optical detection means connected with electronic processing means, said reflectance measuring optical detection means comprising a reflectance measuring detector with an optical window located inside the dyeing tank or machine, a base of the spool being cyclically put in contact with said optical window, periodically, said spool being moved towards the optical window; and
   an actuator, cyclically, moving said pierced axial shaft and said base of the spool towards a part of the dyeing tank or machine where said optical window is located.

2. An apparatus according to claim 1, further comprising an elastic support onto which an edge of said pierced axial shaft is supported.

3. An apparatus according to claim 2, wherein said elastic support has a tubular shape, is coaxial and external to the outlet of said feedpipe and said elastic support has a projection on which the pierced axial shaft is supported.

4. An apparatus according to claim 3, wherein said support comprises a truncated-cone shaped part and a cylindrical part separated from each other by said projection.

5. An apparatus according to claim 1, wherein the actuator comprises a buffer for contacting an edge of said pierced axial shaft.

6. An apparatus according to claim 1, wherein said optical detector has a body with a vertical collar inside the dyeing tank or machine and ending with said optical window, and said optical detector is provided with a lighting optic fiber and, in a position diametrically opposite to the optical window, said optical detector is provided with an optical probe.

7. An apparatus according to claim 1, wherein said optical window is horizontal.

* * * * *